(12) United States Patent
Katashiba

(10) Patent No.: US 9,566,001 B2
(45) Date of Patent: Feb. 14, 2017

(54) OPHTHALMOLOGIC APPARATUS

(71) Applicant: CANON KABUSHIKI KAISHA, Tokyo (JP)

(72) Inventor: Yuji Katashiba, Kawasaki (JP)

(73) Assignee: CANON KABUSHIKI KAISHA, Tokyo (JP)

(*) Notice: Subject to any disclaimer, the term of this patent is extended or adjusted under 35 U.S.C. 154(b) by 0 days.

(21) Appl. No.: 14/858,931

(22) Filed: Sep. 18, 2015

(65) Prior Publication Data

US 2016/0089024 A1     Mar. 31, 2016

(30) Foreign Application Priority Data

Sep. 29, 2014  (JP) .................................. 2014-199179

(51) Int. Cl.
| | | |
|---|---|---|
| *A61B 3/14* | (2006.01) | |
| *A61B 3/10* | (2006.01) | |
| *A61B 3/12* | (2006.01) | |
| *G02B 27/14* | (2006.01) | |

(52) U.S. Cl.
CPC .................. *A61B 3/12* (2013.01); *A61B 3/102* (2013.01); *A61B 3/1025* (2013.01); *A61B 3/14* (2013.01); *G02B 27/141* (2013.01)

(58) Field of Classification Search
USPC ................................................ 351/200–246
See application file for complete search history.

(56) References Cited

U.S. PATENT DOCUMENTS

| | | | | |
|---|---|---|---|---|
| 7,540,614 B2 * | 6/2009 | Kawashima | ............. | A61B 3/14 351/205 |
| 2013/0188144 A1 * | 7/2013 | Makihira | .................. | G01J 4/00 351/221 |

FOREIGN PATENT DOCUMENTS

| | | |
|---|---|---|
| JP | 2009-160190 A | 7/2009 |
| JP | 2014-502552 A | 2/2014 |

* cited by examiner

*Primary Examiner* — Mohammed Hasan
(74) *Attorney, Agent, or Firm* — Canon USA, Inc. IP Division

(57) ABSTRACT

An ophthalmologic apparatus includes a reflective member that reflects light from a first scanning unit that scans an object to be examined with first light and light from a second scanning unit that scans the object with second light having a wavelength different from a wavelength of the first light so as to be applied to the object. The ophthalmologic apparatus includes an optical path synthesis and separation unit that is arranged on two optical paths from the scanning units to the reflective member, and synthesizes two optical paths from the scanning units to the object and separates an optical path of return light from the object into two optical paths on which the scanning units are arranged. A reflection optical path of the optical path synthesis and separation unit is arranged opposite to the object with respect to the optical path synthesis and separation unit.

20 Claims, 7 Drawing Sheets

OPHTHALMOLOGIC APPARATUS

BACKGROUND

Field

Aspects of the present invention generally relate to an ophthalmologic apparatus that images the eye fundus of an eye to be examined.

Description of the Related Art

At present, an imaging apparatus that is capable of capturing a tomographic image of an object to be examined (an eye fundus tomographic image) with high resolution using an optical coherence tomography (OCT) which uses interference caused by low coherent light (hereinbelow, referred to as an OCT apparatus) has been put to practical use. Further, in the ophthalmologic field, a scanning laser ophthalmoscope (SLO, hereinbelow, referred to as an SLO apparatus) that captures an eye fundus surface image of an eye to be examined (a two-dimensional surface image of an object to be examined) with high resolution by laser scanning has been put to practical use. In an eye fundus examination, for the purpose of determining a region in which an eye fundus tomographic image is acquired while observing an eye fundus surface image, it is required to acquire the eye fundus surface image and the eye fundus tomographic image in a desired region on the eye fundus. Japanese Patent Application Laid-Open No. 2009-160190 discloses an ophthalmologic imaging apparatus that branches an optical path by a dichroic mirror to acquire both an eye fundus tomographic image by an OCT apparatus and a two-dimensional eye fundus surface image by an SLO apparatus.

An ophthalmologic imaging apparatus that acquires both an eye fundus tomographic image and an eye fundus surface image typically uses a refractive optical system such as a lens as an objective optical system as in Japanese Patent Application Laid-Open No. 2009-160190. A refractive optical system allows light to enter the objective optical system from the opposite side of an eye to be examined. Thus, it is relatively easy to ensure a space for synthesizing and separating an optical path without interference (contact) with the eye or the face.

In order to prevent symptoms of a small lesion from being overlooked, it is required to acquire an eye fundus tomographic image and an eye fundus surface image in a wide angle-of-view range. In this case, in a refractive optical system, in order to photograph a wide angle-of-view range without increasing the size of an apparatus, it is necessary to reduce the distance (working distance) between an eye to be examined and the optical system. When the working distance is reduced, the nose or the cheek of a subject may interfere (make contact) with the objective optical system or it may be difficult for an operator to perform a photographing support operation such as eyelid opening.

Japanese Patent Application Laid-Open No. 2014-502552 discloses an ophthalmologic imaging apparatus in which an eye to be examined and a scanning reflective mirror (a scanning unit that scans the eye fundus with light) are arranged at two focal points of an objective reflective mirror used as an objective optical system to acquire an eye fundus surface image with a compacter configuration than a refractive optical system as well as in a wide angle-of-view range.

SUMMARY OF THE INVENTION

One ophthalmologic apparatus according to the present invention includes a first light source configured to output first light to be applied to an eye fundus of an eye to be examined, a first scanning unit configured to scan the eye fundus with the first light, a second light source configured to output second light having a wavelength different from a wavelength of the first light, a second scanning unit configured to scan the eye fundus with the second light, a reflective member configured to reflect light from the first scanning unit and light from the second scanning unit to apply the light from the first scanning unit and the light from the second scanning unit to the eye fundus, and an optical path synthesis and separation unit arranged on an optical path from the first scanning unit to the reflective member and on an optical path from the second scanning unit to the reflective member, the optical path synthesis and separation unit being configured to synthesize an optical path from the first scanning unit to the eye fundus with an optical path from the second scanning unit to the eye fundus and separate an optical path of return light from the eye fundus into an optical path on which the first scanning unit is arranged and an optical path on which the second scanning unit is arranged, wherein a reflection optical path of the optical path synthesis and separation unit is arranged opposite to the eye to be examined with respect to the optical path synthesis and separation unit.

Further features of the present disclosure will become apparent from the following description of exemplary embodiments (with reference to the attached drawings).

DESCRIPTION OF THE EMBODIMENTS

Figure 1:
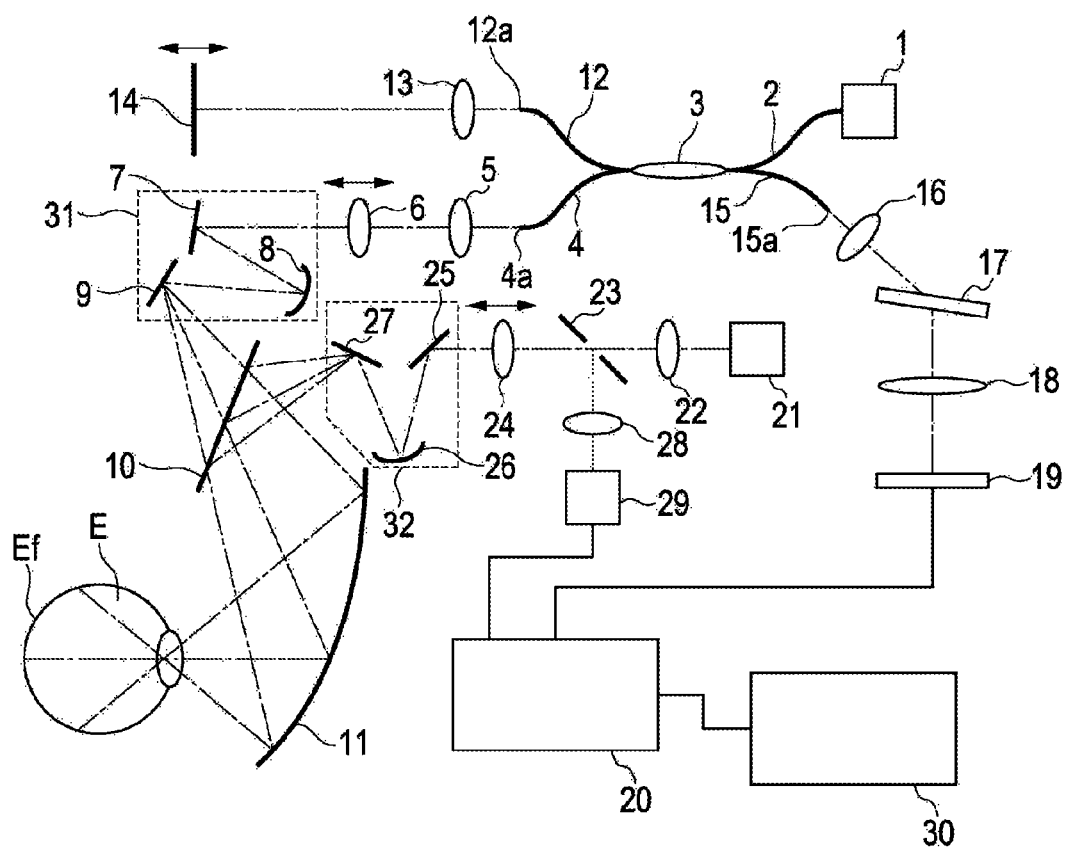
FIG. 1 is a schematic view illustrating an outline of an eye fundus image acquisition apparatus in a first embodiment of the present invention.

Conventionally, there has been no ophthalmologic apparatus that acquires both a tomographic image and a two-dimensional surface image of an eye to be examined and uses a reflective member as an objective optical system. Thus, in ophthalmologic apparatuses that acquire both a tomographic image and a two-dimensional surface image of an eye to be examined, no consideration has, of course, been made for an optimal optical arrangement in an optical system that uses a reflective member as an objective optical system.

One object of an embodiment of the present invention is to achieve an optimal optical arrangement in an optical system that uses a reflective member as an objective optical system in an ophthalmologic apparatus that acquires both a tomographic image and a two-dimensional surface image of an eye to be examined in a wide angle-of-view range while ensuring the distance from the eye to be examined to the objective optical system to some extent.

Thus, an optical apparatus according to an embodiment of the present invention includes a reflective member (an elliptical reflective mirror, for example) that reflects light from a first scanning unit that scans an object to be examined (an eye to be examined, for example) with first light and light from a second scanning unit that scans the object to be examined with second light having a wavelength different from a wavelength of the first light to apply the light from the first scanning unit and the light from the second scanning unit to the object to be examined. The optical apparatus further includes an optical path synthesis and separation unit (a dichroic mirror which is an example of a wavelength separation member, for example) that is arranged on an optical path from the first scanning unit to the reflective member and on an optical path from the second scanning unit to the reflective member. In this case, the optical path synthesis and separation unit synthesizes an optical path from the first scanning unit to the object to be examined (a transmission optical path of the optical path synthesis and separation unit, for example) with an optical path from the second scanning unit to the object to be examined (a reflection optical path of the optical path synthesis and separation unit, for example). Further, the optical path synthesis and separation unit separates an optical path of return light from the object to be examined into an optical path on which the first scanning unit is arranged and an optical path on which the second scanning unit is arranged. Accordingly, it is possible to scan the eye to be examined in a wide angle-of-view range with a plurality of light beams having different wavelengths while ensuring the distance from the eye to be examined to the objective optical system to some extent. Thus, for example, an ophthalmologic apparatus that acquires both a tomographic image and a two-dimensional surface image of the eye to be examined can be provided.

The reflection optical path of the optical path synthesis and separation unit is arranged opposite to the object to be examined with respect to the optical path synthesis and separation unit. Accordingly, in the ophthalmologic apparatus, interference (contact) between the nose or the cheek of a subject and the objective optical system is prevented and it becomes relatively easy for an operator to perform a photographing support operation such as eyelid opening. Thus, it is possible to achieve an optimal optical arrangement in an optical system that uses a reflective member as an objective optical system.

When a reflective optical system such as a mirror is used as an objective optical system, it is necessary to allow light to enter the objective optical system from the same side as an eye to be examined. Thus, an optical path is more likely to interfere (make contact) with the eye or the face than a refractive optical system. Thus, in the present embodiment, it is preferred that a first focal point of the reflective member be formed in an anterior eye portion of the eye to be examined and a second focal point of the reflective member be formed in the first scanning unit arranged on the transmission optical path of the optical path synthesis and separation unit. Further, a third focal point of the reflective member is preferably formed in the second scanning unit arranged on the reflection optical path of the optical path synthesis and separation unit. Accordingly, it is possible to perform scanning with a plurality of light beams having different wavelengths with a compacter configuration than a refractive optical system as well as in a wide angle-of-view range.

The closer to 1 the ellipticity of the elliptical reflective mirror which is an example of the reflective member is (that is, the closer to a circle), the longer the distance between an eye to be examined which is an example of the object to be examined and the elliptical reflective mirror (focal distance) is. In this case, although a configuration in which the interference (contact) between an optical path and the eye or the face hardly occurs can be achieved, it is necessary to make the elliptical reflective mirror relatively large (refer to a first embodiment). On the other hand, the larger the ellipticity of the elliptical reflective mirror is, the shorter the distance between the eye to be examined and the elliptical reflective mirror is. In this case, although the interference (contact) between the optical path and the eye or the face is likely to occur, the elliptical reflective mirror can be made relatively small (refer to a second embodiment). When the ellipticity of the elliptical reflective mirror is too close to 1, the first scanning unit and the second scanning unit interfere (make contact) with each other. Thus, the ellipticity of the elliptical reflective mirror is preferably approximately 1.1 (refer to a third embodiment).

One of the first and second scanning units is preferably a scanning unit of an OCT apparatus. In the OCT apparatus, light from a light source is split into measurement light and reference light by, for example, a beam splitter. The measurement light is applied to an object to be examined, for example, the eye through a measurement optical path. Return light from the object to be examined is multiplexed with the reference light and guided as interference light to a detector through a detection optical path. The return light is reflected light or scattered light that includes information about an interface in a light applying direction with respect to the object to be examined. A tomographic image of the object to be examined can be obtained by detecting the interference light formed from the return light and the reference light by the detector and analyzing the detected interference light. The other one of the first and second scanning units is preferably a scanning unit of an SLO apparatus. In the SLO apparatus, light from a light source is applied to scan the eye to be examined by, for example, a galvanometer mirror. Reflected light from the eye to be examined is separated from an illumination optical path by, for example, an apertured reflectivemirror and guided to the detector. A two-dimensional surface image of the eye to be examined can be obtained by detecting the intensity of the reflected light by the detector. Hereinbelow, embodiments of the present invention will be described in detail with reference to the drawings.

First Embodiment

Distance between Object to be Examined and Reflective Member is Long

A first embodiment of the present invention will be described with reference to FIGS. 1 to 5. For example, a surface image and a tomographic image of the retina of a human can be captured by the apparatus of the present embodiment.

(Apparatus Configuration)

An eye fundus image acquisition apparatus which is an example of an ophthalmologic apparatus according to the present embodiment will be described with reference to FIG. 1. A first light source 1 in the present embodiment is a light source for generating first light (low coherence light). In the present embodiment, a super luminescent diode (SLD) light source having a center wavelength of 850 nm and a band of 50 nm is used as the light source 1. An amplified spontaneous emission (ASE) light source may also be applied to the light source 1. Further, an ultra short pulse laser light source such as a titanium sapphire laser may also be applied to the light source 1. In this manner, the light source 1 may be any light source that is capable of generating low coherence light. A wavelength of light generated from the light source 1 is not particularly limited to any wavelength, but selected within the range of 400 nm to 2 μm depending on an object to be examined. The broader a wavelength band is, the higher vertical resolution is. Typically, when the center wavelength is 850 nm, the vertical resolution is 6 μm in a band of 50 nm and 3 μm in a band of 100 nm.

Light emitted from the light source 1 is guided to a light branch unit 3 by a light guide unit 2. For example, a fiber coupler may be applied to the light branch unit 3 which is an example of a splitting unit. The ratio of branching is appropriately selected in accordance with an object to be examined.

A collimator lens 5, a focus lens 6, a scanning reflective mirror 7, an elliptical reflective mirror 8, a scanning reflective mirror 9, a wavelength branch member 10, and an objective elliptical reflective mirror 11 are arranged on an optical path branched toward a light guide unit 4 by the light branch unit 3 to constitute a sample arm. The scanning reflective mirror 7 and the scanning reflective mirror 9 are arranged at two focal positions of the elliptical reflective mirror 8 to constitute a scanning unit 31 which is an example of a first scanning unit. For example, galvanometer mirrors or resonant mirrors which perform scanning with light in X and Y directions perpendicular to each other are applied to the scanning reflective mirror 7 and the scanning reflective mirror 9. The wavelength branch member 10 (wavelength separation member) which is an example of an optical path synthesis and separation unit transmits light emitted from the light source 1 (wavelength: λ=800 to 900 nm). For example, a dichroic mirror which is formed of a multilayer film is applied to the wavelength branch member 10. Light guided to the light guide unit 4 passes through the sample arm, is then reflected by the objective elliptical reflective mirror 11 which is an example of a reflective member, and reaches an eye fundus Ef of an eye E to be examined. The scanning unit 31 may have a configuration in which the scanning reflective mirror 7 and the scanning reflective mirror 9 are arranged close to each other without using the elliptical reflective mirror 8. In this case, the scanning reflective mirror 7 and the scanning reflective mirror 9 are arranged near a light collection position of the objective elliptical reflective mirror 11. That is, the scanning reflective mirror 7 and the scanning reflective mirror 9 are arranged at optically substantially conjugate positions with respect to an anterior eye portion of the eye E to be examined. The scanning reflective mirror 7 and the scanning reflective mirror 9 may be configured as an integrated scanning member.

A collimator lens 13 and a reference reflective mirror 14 are arranged on an optical path branched toward a light guide unit 12 by the light branch unit 3 to constitute a reference arm. The reference reflective mirror 14 is arranged on a linear motion stage (not illustrated). An optical path length of the reference arm is adjusted by moving the linear motion stage in an optical axis direction.

A lens 16, a spectroscopic unit 17 which includes a grating as a diffractive grating and a prism, an imaging lens 18, and a detection unit 19 which includes a photoelectric conversion element such as a CMOS or a CCD constitute a spectroscope. Light from the light branch unit 3 is guided to the spectroscope by a light guide unit 15 which is connected to the light branch unit 3. The detection unit 19 is an example of a first detection unit.

On the other hand, a second light source 21 in the present embodiment is a light source for generating second light having a wavelength different from a wavelength of the first light from the first light source 1. In the present embodiment, a light-emitting diode (LED) light source having a center wavelength of 780 nm is used as the light source 21. A laser diode (LD) light source may also be applied to the light source 21. In this manner, the light source 21 may be any light source that is capable of generating light having a wavelength different from the wavelength of light generated by the light source 1.

A collimator lens 22, an apertured reflectivemirror 23, a focus lens 24, a scanning reflective mirror 25, an elliptical reflective mirror 26, a scanning reflective mirror 27, the wavelength branch member 10, and the objective elliptical reflective mirror 11 are arranged on an optical path of light ejected from the light source 21.

Light from the light source 21 passes through a hole formed on an optical axis of the apertured reflectivemirror 23. The scanning reflective mirror 25 and the scanning reflective mirror 27 are arranged at two focal positions of the elliptical reflective mirror 26 to constitute a scanning unit 32 which is an example of a second scanning unit. For example, galvanometer mirrors or resonant mirrors which perform scanning with light in X and Y directions perpendicular to each other are applied to the scanning reflective mirror 25 and the scanning reflective mirror 27. The wavelength branch member 10 reflects light emitted from the light source 21 (wavelength: λ=780 nm). The light reflected by the wavelength branch member 10 is reflected by the objective elliptical reflective mirror 11 and reaches the eye fundus Ef of the eye E to be examined. The scanning unit 32 may have a configuration in which the scanning reflective mirror 25 and the scanning reflective mirror 27 are arranged close to each other without using the elliptical reflective mirror 26. In this case, the scanning reflective mirror 25 and the scanning reflective mirror 27 are arranged near the light collection position of the objective elliptical reflective mirror 11. That is, the scanning reflective mirror 25 and the scanning reflective mirror 27 are arranged at optically substantially conjugate positions with respect to the anterior eye portion of the eye E to be examined. The scanning reflective mirror 25 and the scanning reflective mirror 27 may be configured as an integrated scanning member.

Further, light reflected by the eye funds Ef returns along the same optical path as the optical path during the entry to the eye funds and is then reflected by a peripheral part of the apertured reflectivemirror 23. An imaging lens 28 and a detection unit 29 which includes a photoelectric conversion element such as an APD are arranged on an optical path of light reflected by the apertured reflectivemirror 23. The detection unit 29 is an example of a second detection unit.

A control unit 20 controls the linear motion stage (not illustrated) on which the reference reflective mirror 14 is arranged, the detection unit 19, and the detection unit 29. A display unit 30 is connected to the control unit 20.

(Optical System Configuration)

Next, the configuration of the optical system in the first embodiment will be described in more detail with reference to FIG. 2. An optical path from a light source to a scanning unit is not illustrated in FIG. 2.

A scanning unit 31A includes a scanning reflective mirror 7A, an elliptical reflective mirror 8A, and a scanning reflective mirror 9A. The scanning unit 31A is arranged on a transmission optical path of a wavelength branch member 10A. The scanning reflective mirror 7A and the scanning reflective mirror 9A are arranged at two focal positions of the elliptical reflective mirror 8A. Further, the scanning reflective mirror 9A is arranged at one of two focal positions (a second focal position) of an objective elliptical reflective mirror 11A. The eye E to be examined E (not illustrated) is arranged at the other focal position (a first focal position) of the objective elliptical reflective mirror 11A. The scanning reflective mirror 7A, the scanning reflective mirror 9A, and the position of a pupil of the eye E to be examined are arranged at optically conjugate positions with each other. Thus, a desired position on the eye fundus Ef can be two-dimensionally scanned by performing scanning with light by each of the scanning reflective mirrors.

A scanning unit 32A includes a scanning reflective mirror 25A, an elliptical reflective mirror 26A, and a scanning reflective mirror 27A. The scanning unit 32A is arranged on a reflection optical path of the wavelength branch member 10A. The scanning reflective mirror 25A and the scanning reflective mirror 27A are arranged at two focal positions of the elliptical reflective mirror 26A. Further, the scanning reflective mirror 27A is arranged at a focal position (third focal position) of the objective elliptical reflective mirror 11A formed by light reflected by the wavelength branch member 10A. As described above, the eye E to be examined is arranged at another focal position (first focal position) of the objective elliptical reflective mirror 11A. The scanning reflective mirror 25A, the scanning reflective mirror 27A, and the position of the pupil of the eye E to be examined are arranged at optically conjugate positions with each other. Thus, a desired position on the eye fundus Ef can be two-dimensionally scanned by performing scanning with light by each of the scanning reflective mirrors.

The wavelength branch member 10A is arranged within an optical path extending from the scanning unit 31A to the objective elliptical reflective mirror 11A and on an optical path extending from the scanning unit 32A to the objective elliptical reflective mirror 11A. Light from the scanning unit 31A and light from the scanning unit 32A are synthesized into an optical path of the same optical system. The synthesized light enters the eye fundus Ef of the eye E to be examined through the objective elliptical reflective mirror 11A. Further, light reflected by the eye fundus Ef and then reflected by the objective elliptical reflective mirror 11A is separated into optical paths of different optical systems by the wavelength branch member 10A. This enables the scanning unit 31A and the scanning unit 32A to independently and simultaneously scan a desired position on the eye fundus Ef.

When the eye E to be examined is arranged at one focal point of the objective elliptical reflective mirror 11A and the scanning unit 31A is arranged at the other focal point thereof, it is necessary to ensure the distance between the two focal points so as to avoid spatial interference between the head of a subject and the scanning unit 31A. When a certain distance between the focal points is ensured and the ellipticity of the objective elliptical reflective mirror 11A is reduced, the distance between the eye E to be examined and a reflection surface of the objective elliptical reflective mirror 11A is increased and an optical effective region required for the objective elliptical reflective mirror 11A is enlarged. Thus, reducing the ellipticity makes it easier to ensure a longer distance (working distance) between the eye E to be examined and the reflection surface of the objective elliptical reflective mirror 11A. A long working distance is advantageous in arranging the optical system without interference with the nose or the cheek of a subject. On the other hand, when the ellipticity of the objective elliptical reflective mirror 11A is increased, the distance between the eye E to be examined and the reflection surface of the objective elliptical reflective mirror 11A is reduced and the optical effective region required for the objective elliptical reflective mirror 11A is reduced. When the objective elliptical reflective mirror 11A becomes small, the distance between the focal point at which the scanning unit 31A is arranged and the reflection surface of the objective elliptical reflective mirror 11A is increased. This makes it easy to arrange the two scanning units and the wavelength branch member 10A without spatial interference therebetween. Thus, a large ellipticity is advantageous in arranging the scanning unit 31A, the scanning unit 32A, the wavelength branch member 10A, and the objective elliptical reflective mirror 11A within a compacter space without spatial interference therebetween.

In the optical system of the present invention, the ellipticity a/b of the objective elliptical reflective mirror 11 preferably satisfies the following Expression (1).

$$1.1 < a/b < 2.4 \tag{1}$$

In Expression (1), a denotes the major axis of the elliptical shape of the reflection surface of the objective elliptical reflective mirror 11 and b denotes the minor axis thereof. The major axis a is the length between two intersection points between a straight line that passes through the two focal points of the objective elliptical reflective mirror 11 and an ellipse that is formed by extending the reflection surface shape up to the outside of the optical effective region. The minor axis b is the length between two intersection points between a straight line that passes through the middle point of a straight line connecting the two focal points of the objective elliptical reflective mirror 11 and is perpendicular to the major axis a and the ellipse that is formed by extending the reflection surface shape up to the outside of the optical effective region. That is, the reflection surface of the objective elliptical reflective mirror 11 is an ellipse having the major axis a and the minor axis b and a part of a spheroid that is rotationally symmetric with respect to the major axis a.

When the ellipticity a/b exceeds the lower limit of Expression (1), the objective elliptical reflective mirror 11 is enlarged, and a space for arranging the two scanning units and the wavelength branch member 10 is narrowed. Thus, it becomes difficult to arrange the scanning reflective mirrors and a driving mechanism without spatial interference therebetween. On the other hand, the ellipticity a/b exceeds the upper limit of Expression (1), the distance between the eye E to be examined and the reflection surface of the objective elliptical reflective mirror 11 is reduced, and the optical system is likely to interfere with the nose or the cheek of a subject. Thus, it becomes difficult to acquire an image of a desired photographing region. Therefore, the ellipticity exceeding the upper limit of Expression (1) is not preferred.

When two optical paths are synthesized and separated by the wavelength branch member 10, the wavelength branch member 10 is required to be arranged at a position that does not obstruct a path of light that enters the eye E to be examined from the objective elliptical reflective mirror 11. Further, it is necessary to ensure a space for arranging each element so as to prevent spatial interference between the scanning reflective mirrors of the scanning unit 31 and the scanning unit 32 and the driving mechanism. Further, an optical path extending from the scanning unit 32 to the wavelength branch member 10 is required not to spatially interfere with the objective elliptical reflective mirror 11.

In the optical system of the present invention, an angle α between a reflection surface of the wavelength branch member 10 and the straight line that passes through the two focal points of the objective elliptical reflective mirror 11 preferably satisfies the following Expression (2).

$$-7° < \alpha < 55° \qquad (2)$$

Figure 2:
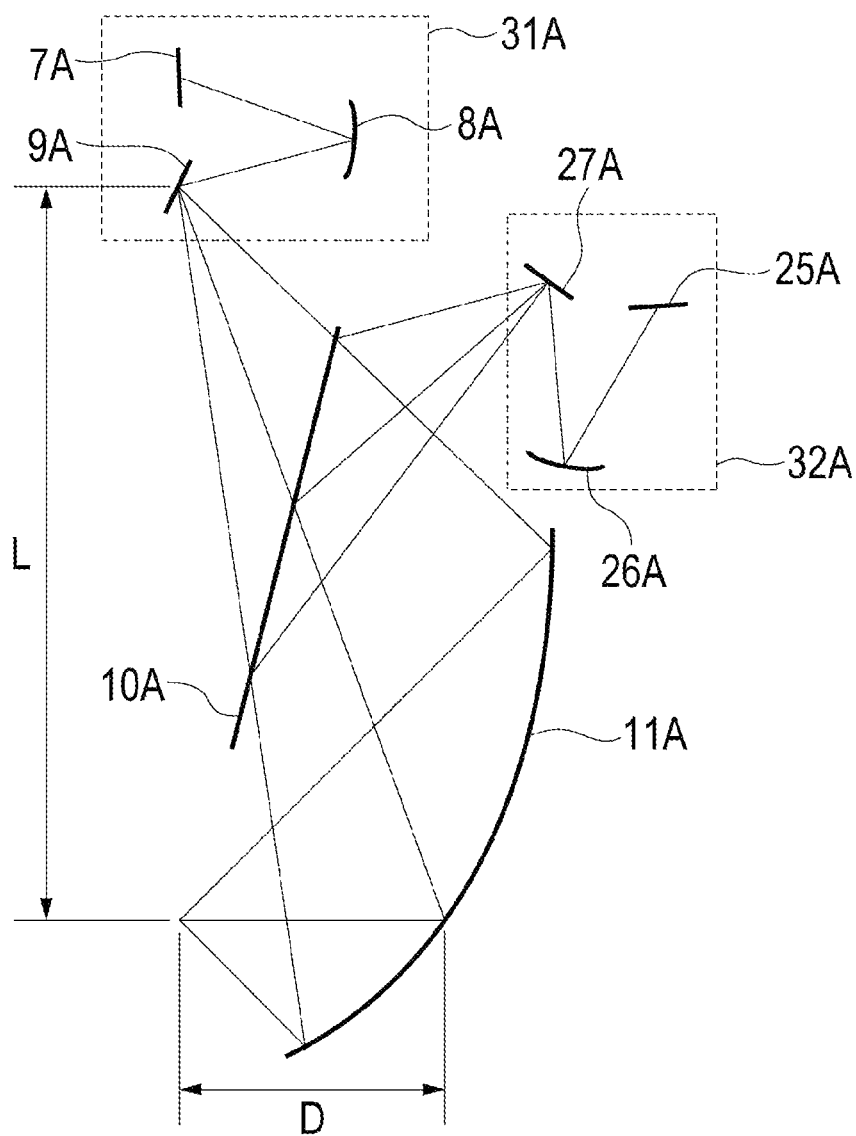
FIG. 2 is a diagram illustrating the configuration of an optical system in the first embodiment of the present invention.

In the sign of α, when an intersection point between a straight line that passes through the two focal points of the objective elliptical reflective mirror 11 and a straight line that is formed by extending the reflection surface of the wavelength branch member 10 up to the outside of the optical effective region is defined as a rotation center in FIG. 2, clockwise rotation is positive based on the straight line that passes through the two focal points.

When the angle α exceeds the lower limit of Expression (2), the distance between the wavelength branch member 10 and the scanning unit 31 is reduced and the distance between the scanning unit 31 and the scanning unit 32 is also reduced. Thus, it becomes difficult to arrange the scanning reflective mirrors and the driving mechanism without spatial interference therebetween. On the other hand, when the angle α exceeds the upper limit of Expression (2), the distance between an optical path extending from the scanning unit 32 to the wavelength branch member 10 and the objective elliptical reflective mirror 11 is reduced. Further, as the angle of view of the objective elliptical reflective mirror 11 is increased, the distance between the optical path extending from the scanning unit 32 to the wavelength branch member 10 and the objective elliptical reflective mirror 11 is further reduced. Thus, it becomes difficult to arrange each element without spatial interference between the optical path extending from the scanning unit 32 to the wavelength branch member 10 and the objective elliptical reflective mirror 11 while ensuring a wide angle-of-view range. Therefore, the angle α exceeding the upper limit of Expression (2) is not preferred.

The optical system of the present invention is suitable for photographing a region on the eye fundus in a wide angle-of-view range by satisfying Expressions (1) and (2). For example, the optical system of the present invention is suitable for photographing a wide angle-of-view range, specifically, when the angle range of light entering the eye E to be examined is 55° or more.

In the present embodiment, the ellipticity of the reflection surface shape of the objective elliptical reflective mirror 11A is a/b=1.40 and thus satisfies Expression (1). Further, the angle of the wavelength branch member 10A is α=14° and thus satisfies Expression (2). Accordingly, it is possible to arrange the wavelength branch member 10A between the objective elliptical reflective mirror 11A and the scanning units 31A and 32A without spatial interference therebetween.

In the present embodiment, the distance between the two focal points of the objective elliptical reflective mirror 11A is L=200 mm, and the distance from the focal point of the objective elliptical reflective mirror 11A at which the eye E to be examined is arranged to the reflection surface is D=73 mm. The angle-of-view range of light entering the eye E to be examined is 90°.

In this manner, the optical system of the present embodiment is capable of simultaneously scanning two different regions on the eye fundus Ef over a wide angle-of-view range while ensuring a long working distance.

(Measurement Method)

Next, a method for acquiring a retina image of the eye fundus Ef of the eye E to be examined using the apparatus having such a configuration will be described with reference to FIG. 1.

The eye E to be examined is arranged in front of the apparatus. Then, the control unit 20 turns on the light source 21 in response to an instruction from an operator. At this point, the control unit 20 drives the scanning reflective mirror 25 and the scanning reflective mirror 27 to two-dimensionally scan and illuminate the eye E to be examined with light from the light source 21.

Light from the light source 21 is converted to parallel light by the collimator lens 22 and passes through the hole formed on the optical axis of the apertured reflectivemirror 23. Further, the light that has passed through the hole passes through the focus lens 24, is then sequentially reflected by the scanning reflective mirror 25, the elliptical reflective mirror 26, the scanning reflective mirror 27, the wavelength branch member 10, and the objective elliptical reflective mirror 11, and thereby enters the anterior eye portion of the eye E to be examined.

Reflected light from the anterior eye portion illuminated in this manner returns along the same optical path as the optical path during the entry, is then reflected by the peripheral part of the apertured reflectivemirror 23, and is then imaged on a detection surface of the detection unit 29 by the lens 28. A video image signal from the detection unit 29 (a detection result detected by the second detection unit) is input to the control unit 20 which is an example of a second image forming unit and converted to digital data in real time to generate an anterior eye portion image.

The center of a photographing surface and the optical axis of the imaging optical system are adjusted to be aligned with each other. Thus, the amount of eccentricity between a pupil center of the anterior eye portion image captured by the detection unit 29 and the photographing center corresponds to the amount of eccentricity between the eye E to be examined and the imaging optical system. The imaging optical system is arranged on a stage (not illustrated) in such a manner that the position of the imaging optical system is adjustable in upper, lower, right and left directions and also in an optical axis direction with respect to the eye E to be examined. The anterior eye portion image is displayed on the display unit 30. An operator drives the stage while confirming the displayed image to adjust the upper, lower, right and left positions so as to align the pupil center with the optical axis.

After the upper, lower, right and left positions are adjusted, position adjustment in the optical axis direction is performed so as to align a pivot point which is a reference point on which light beams of the respective angles of view to be scanned are collected with the pupil position of the eye E to be examined. An eye fundus image which is a second image in the present embodiment is displayed on the display unit 30 by adjusting the position of the imaging optical system in the optical axis direction to reduce the working distance. An operator drives the stage while confirming the fundus image to adjust the position in the optical axis direction so as to reduce vignetting on the peripheral part of the eye fundus image.

After the adjustment of the position in the optical axis direction, a focus position is adjusted so that the eye fundus Ef is in focus. The focus lens 24 is arranged on a stage (not illustrated) in such a manner that the position of the focus lens 24 is adjustable in the optical axis direction. When the position of the focus lens 24 is driven in the optical axis direction, the focus position of the imaging optical system changes. An operator drives the stage while confirming the image displayed on the display unit 30 to adjust the position of the focus lens 24 so as to make the brightness or the contrast of the image highest. At this point, control position information of the focus lens 24 is always stored in a memory by the control unit 20.

After the completion of the above adjustment, the control unit 20 turns on the light source 1 in response to an instruction from an operator and drives the scanning reflective mirror 7 and the scanning reflective mirror 9 to two-dimensionally scan the eye fundus Ef of the eye E to be examined with light.

Light from the light source 1 is guided to the light branch unit 3 by the light guide unit 2 and branched in such a manner that the ratio between the amount of light guided to the light guide unit 4 and the amount of light guided to the light guide unit 12 is, for example, 1:9. Light guided to the light guide unit 4 reaches a fiber end 4a. Light emitted from the fiber end 4a as a point light source is converted to parallel light by the collimator lens 5 and passes through the focus lens 6. Then, the light is sequentially reflected by the scanning reflective mirror 7, the elliptical reflective mirror 8 and the scanning reflective mirror 9, then passes through the wavelength branch member 10, is then reflected by the objective elliptical reflective mirror 11, and thereby enters the eye fundus Ef through the pupil of the eye E to be examined.

The focus lens 6 is arranged on a stage (not illustrated) in such a manner that the position of the focus lens 6 is adjustable in the optical axis direction. The memory stores therein the control position information of the focus lens 24 and information of the relationship between the position of the focus lens 24, the position of the focus lens 6, and focus positions of the respective optical systems. Thus, the position of the focus lens 6 is adjusted on the basis of the control position information of the focus lens 24 stored during the focus adjustment using these pieces of information.

Return light reflected and scattered by a plurality of layers that constitute the retina of the eye fundus Ef returns along the same optical path as the optical path during the entry, passes through the collimator lens 5, and then enters the light guide unit 4 through the fiber end 4a so as to be guided to the light branch unit 3. The light branch unit 3 branches the light in such a manner that the ratio between the amount of light guided to the light guide unit 2 and the amount of light guided to the light guide unit 15 is 1:9.

On the other hand, light guided to the light guide unit 12 by the light branch unit 3 is emitted from a fiber end 12a, then converted to parallel light by the lens 13, and then travels to the reference reflective mirror 14. The reference reflective mirror 14 is arranged perpendicular to the parallel light and arranged on a linear motion stage (not illustrated) which is movable in the optical axis direction. Accordingly, the length of the reference optical path and the length of the measurement optical path can be adjusted even with respect to eyes E to be examined having different axial lengths. Reference light reflected by the reference reflective mirror 14 is collected on the fiber end 12a of the light guide unit 12 by the lens 13, then guided to the light branch unit 3 by the light guide unit 12, and then branched into the light guide unit 2 and the light guide unit 15. The branching ratio at this point is 9:1 which is the reverse of the ratio in the return light from the eye E to be examined.

Light guided to the light guide unit 15 which is an interference light generation unit in the present embodiment forms combined light with the return light from the eye fundus Ef. The combined light is converted to parallel light by the collimator lens 16 and then enters the spectroscopic unit 17. Many diffractive gratings having a size closer to the wavelength of light are formed at regular intervals on the spectroscopic unit 17 to disperse the incident light by diffraction. The diffraction angle differs depending on the wavelength. Thus, the diffracted light is imaged as a liner image on a linear light receiving region of the detection unit 19 by the imaging lens 18. That is, light emitted from the fiber end 15a is imaged as a dispersed slit image. Thus, the detection unit 19 outputs a signal corresponding to the intensity of each wavelength.

A signal from the detection unit 19 (a detection result detected by the first detection unit) is input to the control unit 20 which is an example of a first image forming unit, and a tomographic image which is a first image in the present embodiment is generated and displayed on the display unit 30. An operator performs position adjustment (coherence gate adjustment) for the reference reflective mirror 14 so as to position the tomographic image of a target region in a desired region on a display region while looking at the brightness of the tomographic image displayed on the display unit 30. The control unit 20 moves the position of the linear motion stage in response to an instruction from an operator and changes control position information of the linear motion stage stored in a memory (not illustrated) in accordance with the movement amount. The linear motion stage is controlled to drive by a stepping motor (not illustrated). The position of the linear motion stage corresponds to the number of steps instructed to the stepping motor. For example, when a stroke of 60 mm is driven by 60,000 steps, the movement amount per one step is 1 μm. Steps from 0 to 60,000 correspond to the positions of the linear stage from 0 to 60 mm. The distance between a reference position of the linear stage to the lens 13 is accurately set in design and the relationship between the reference position and the stage position is obvious in design. Thus, the reference optical path length can be calculated from the number of steps. In this manner, the length of the reference optical path changes along with a change in the position of the reference reflective mirror 14. Accordingly, the position of the tomographic image displayed in the display region changes. The position of the reference reflective mirror 14 is always stored in the memory. After the above preparation for photographing, still image capturing of the tomographic image is performed upon receiving an instruction through a photographing button (not illustrated). Accordingly, the captured tomographic image is stored in the memory.

(Tomographic Image Generation)

Next, generation of a tomographic image will be described.

During tomographic image capturing, combined light formed from return light from the eye fundus Ef of the eye E to be examined and reference light reflected by the reference reflective mirror 14 is guided to the light guide unit 15. The return light and the reference light has a phase difference when multiplexed by the light branch unit 3 due to the difference between an optical path length from the light branch unit 3 to the eye fundus Ef and an optical path length from the light branch unit 3 to the reference reflective mirror 14. The phase difference differs depending on the wavelength. Thus, interference fringes are generated in spectral intensity distribution present on the light receiving region of the detection unit 19. Since the retina has a plurality of layers and return light beams from the boundaries between the layers have different optical path lengths, the interference fringes include interference fringes of different frequencies. The position of a reflecting object and the brightness corresponding to reflection/scattering from the position of the reflecting object can be obtained from the frequencies of the interference fringes included in the intensity distribution and intensities thereof.

In a B scan mode for scanning one line on the eye fundus, the control unit 20 reads output from the detection unit 19 while driving only one of the X, Y scanning reflective mirrors, specifically, the scanning reflective mirror 7 and the scanning reflective mirror 9, for example, driving only the X scanning reflective mirror. Data indicating the angle of the scanning mirror is output from the scanning reflective mirror 7 or the scanning reflective mirror 9. The read signal is converted to digital data together with the angle of the scanning reflective mirror, further converted to an angle $\theta i$ of light entering the eye E to be examined, and stored in the memory. The angle of scanning reflective mirror and the entry angle $\theta i$ of a light beam correspond to each other, and are obtained from a design value of the optical system.

Figure 3:
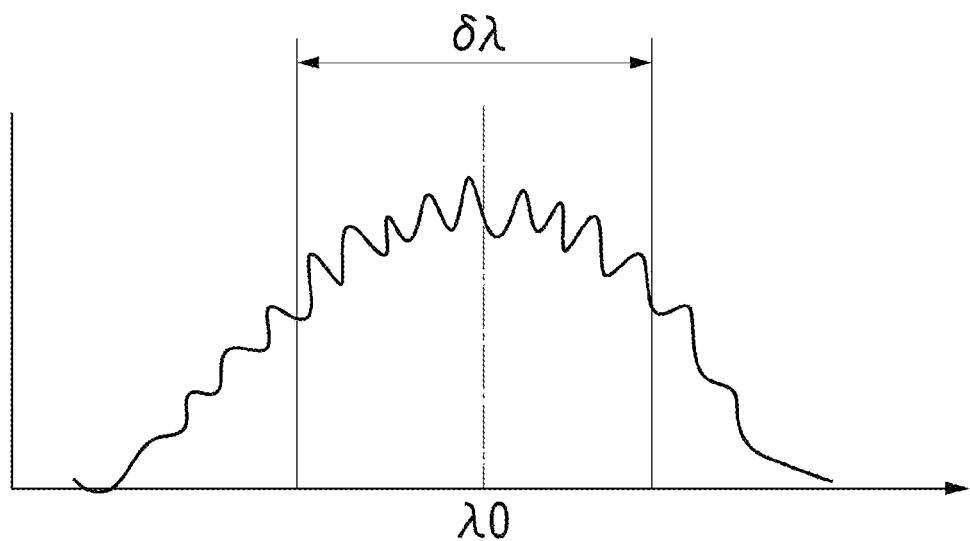
FIG. 3 is a diagram illustrating the shape of a signal in the first embodiment of the present invention.

FIG. 3 illustrates the intensity distribution of light on the detection unit 19 in the angle $\theta i$ of the scanning reflective mirror. The horizontal axis represents the sensor position on the detection unit 19 and corresponds to the wavelength. The vertical axis represents the signal intensity. In FIG. 3, a waveform of interference fringes overlaps the intensity distribution with a center wavelength of $\lambda 0$ and a half-value width of $\delta\lambda$.

Figure 4:
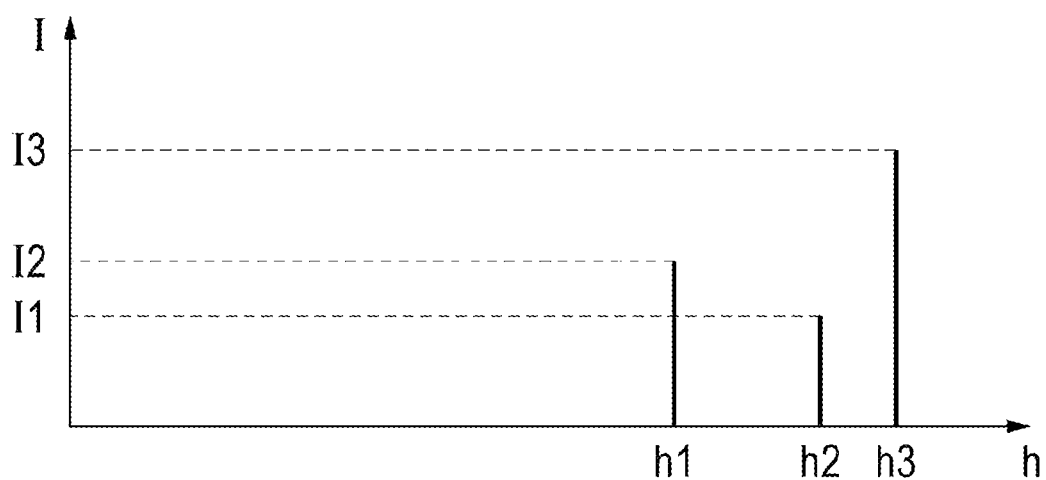
FIG. 4 is a diagram illustrating an output signal in the first embodiment of the present invention.
Figure 5:
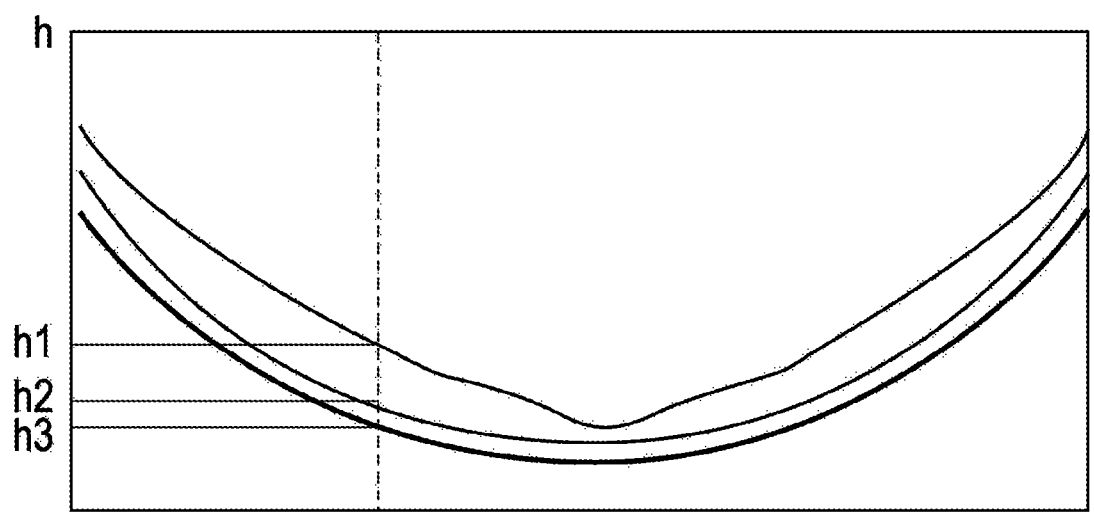
FIG. 5 is a diagram illustrating a tomographic image of the first embodiment of the present invention.

Intensity information of this waveform is read, converted to digital data by an A/D converter, and stored in the memory. When the data is frequency-converted, the intensity distribution as illustrated in FIG. 4 is obtained. FIG. 4 shows that the interference intensities at distances h1, h2, and h3 (the distance from the coherence gate) are respectively I1, I2, and I3. Thus, the interference intensity is measured while changing the angle $\theta i$ of a scan mirror from $\theta s$ to $\theta e$. The interference intensity I ($\theta i$, hj) acquired in this manner is displayed with the horizontal axis of $\theta$ and the vertical axis of h. As a result, a B scan image (an image based on an optical distance) of the eye fundus can be displayed as illustrated in FIG. 5.

In this manner, the present embodiment enables an eye fundus surface image and an eye fundus tomographic image to be simultaneously acquired in the respective desired photographing regions over a wide angle-of-view range by using the elliptical reflective mirror as the objective optical system and arranging the wavelength branch member between the objective elliptical reflective mirror and the two scanning units.

Second Embodiment

Figure 6:
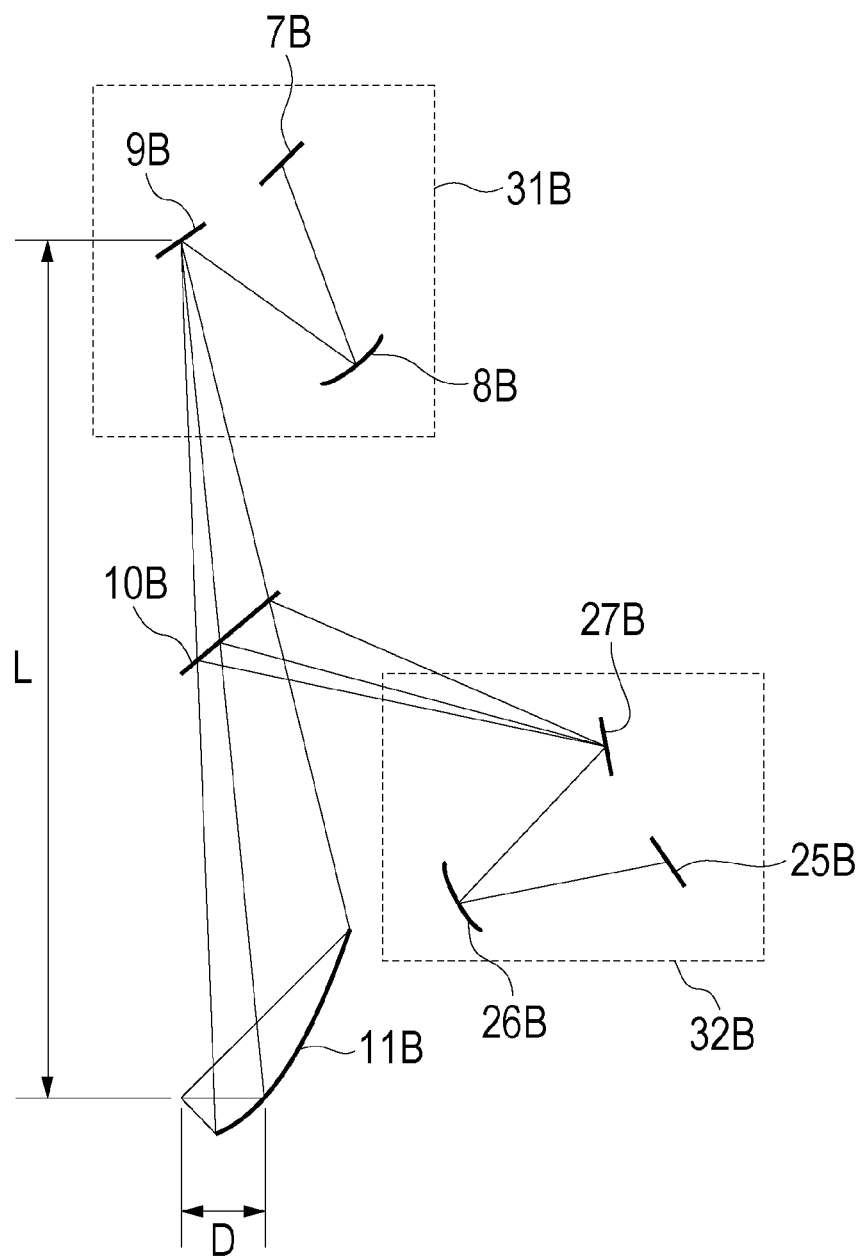
FIG. 6 is a diagram illustrating the configuration of an optical system in a second embodiment of the present invention.

Distance Between Object to be Examined and Reflective Member is Short, but Reflective Member is Relatively Small Next, a second embodiment will be described with reference to FIG. 6. FIG. 6 illustrates the configuration of an optical system of the present embodiment in which an optical path from a light source to a scanning unit is omitted. In the present embodiment, an ellipticity a/b of the shape of an objective elliptical reflective mirror 11B is a/b=2.35 and thus satisfies Expression (1). An angle $\alpha$ between a reflection surface of a wavelength branch member 10B and a straight line that passes through two focal points of the objective elliptical reflective mirror 11B is $\alpha$=50° and thus satisfies Expression (2). Accordingly, it is possible to configure the objective elliptical reflective mirror 11B, the wavelength branch member 10B, a scanning unit 31B, and a scanning unit 32B without spatial interference therebetween.

In the present embodiment, the distance between the two focal points of the objective elliptical reflective mirror 11B is L=200 mm. The distance between the focal point of the objective elliptical reflective mirror 11B at which an eye E to be examined (not illustrated) is arranged and the reflection surface is D=20 mm. A angle-of-view range of light entering the eye E to be examined is 90°.

In the present embodiment, the ellipticity of the objective elliptical reflective mirror 11B is made larger than that in the first embodiment. This configuration enables two different desired photographing regions on the eye fundus to be simultaneously scanned over a wide angle-of-view range with a compacter optical system.

Third Embodiment

First Scanning Unit and Second Scanning Unit are Close to Each Other

Figure 7:
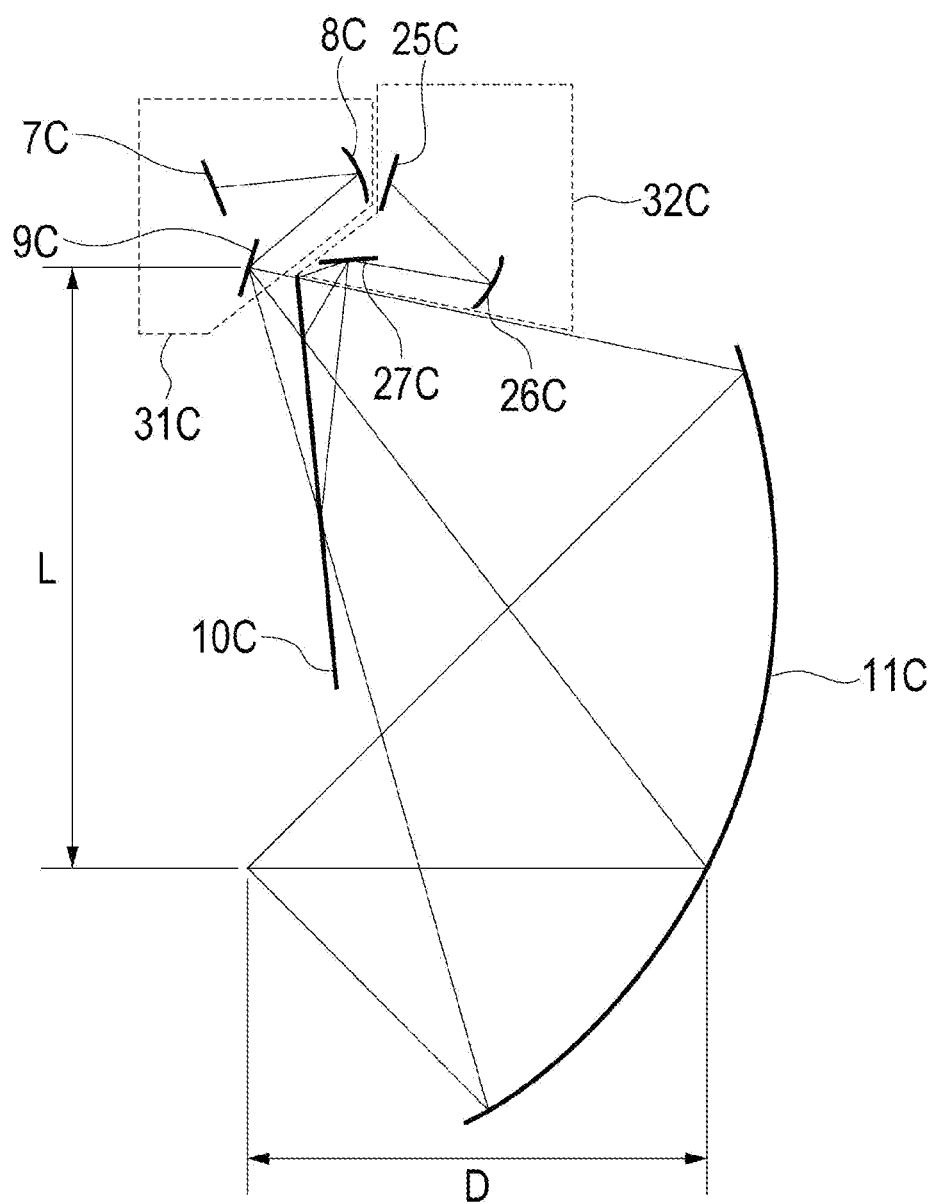
FIG. 7 is a diagram illustrating the configuration of an optical system in a third embodiment of the present invention.

A third embodiment will be described with reference to FIG. 7. FIG. 7 illustrates the configuration of an optical system of the present embodiment in which an optical path from a light source to a scanning unit is omitted. In the present embodiment, an ellipticity a/b of the shape of an objective elliptical reflective mirror 11C is a/b=1.15 and thus satisfies Expression (1). An angle $\alpha$ between a reflection surface of a wavelength branch member 10C and a straight line that passes through two focal points of the objective elliptical reflective mirror 11C is $\alpha$=−6° and thus satisfies Expression (2). Accordingly, it is possible to configure the objective elliptical reflective mirror 11C, the wavelength branch member 10C, a scanning unit 31C, and a scanning unit 32C without spatial interference therebetween.

In the present embodiment, the distance between the two focal points of the objective elliptical reflective mirror 11C is L=200 mm. The distance between the focal point of the objective elliptical reflective mirror 11C at which an eye E to be examined (not illustrated) is arranged and the reflection surface is D=153 mm. A angle-of-view range of light entering the eye E to be examined is 90°.

In the present embodiment, the ellipticity of the objective elliptical reflective mirror 11C is made smaller than that in the first embodiment. This configuration enables two different desired photographing regions on the eye fundus to be simultaneously scanned over a wide angle-of-view range while ensuring a longer working distance.

Other Embodiments

The preferred embodiments of the present invention have been described above. However, it is needless to say that the present invention is not limited to these embodiments and various modifications and changes may be made within the subject matter of the present invention.

For example, in each of the optical systems of the first to third embodiments, the two focal points of the elliptical reflective mirror of the scanning unit are arranged at optically conjugate positions with the pupil of the eye E to be examined, and the scanning reflective mirrors are arranged at the respective focal positions. Alternatively, no elliptical reflective mirror may be arranged in the scanning unit, and two scanning reflective mirrors may be arranged in front and rear of a position on an optical path that is optically conjugate with the pupil. In this case, no elliptical reflective mirror is required in the scanning unit. Thus, an optical system having a simpler configuration can be achieved.

The light source 21 may include a plurality of wavelengths, for example, by synthesizing optical paths of light beams from a plurality of light sources having different wavelengths by a dichroic mirror. For example, a color image of the eye fundus Ef can be acquired by applying visible RGB light to the eye fundus Ef, and detecting and processing light of each wavelength reflected by the eye fundus Ef. In this case, reflective mirrors are mainly included from the scanning unit to the objective elliptical reflective mirror 11. Since chromatic aberration is not generated in a reflective mirror, this configuration is advantageous in a reduction of chromatic aberration in the optical system. Thus, a difference in image quality between RGB images caused by chromatic aberration can be reduced, which is advantageous in acquiring a color image of higher quality. Further, in this case, an index (fixation lamp) for guiding the direction of the eye of a subject may be lighted at any position in a scanning region by turning on or off a visible light source at scanning timing of the scanning unit 32. This configuration is capable of reducing the movement of the eye during photographing and thus advantageous in acquiring an image of higher quality.

Further, an excitation light source for fluorescent eye fundus may be arranged on the light source 21, and a barrier filter that blocks excitation light, but transmits fluorescent light may be arranged between the apertured reflectivemirror 23 and the detection unit 19. In this case, it is possible to acquire a fluorescent contrast image of the eye fundus Ef over a wide angle-of-view range.

In the first embodiment, a spectral-domain OCT (SD-OCT) system which uses a broad band light source and a spectroscope is applied to a system that acquires a tomographic image. Alternatively, a swept-source OCT (SS-OCT) system which uses a wavelength tunable light source may be applied. In the first embodiment, a surface image is acquired on an optical path in which return light from the eye fundus Ef is reflected by the wavelength branch member 10 and a tomographic image is acquired on an optical path in which the return light is transmitted. On the contrary, a tomographic image may be acquired on the optical path in which the return light is reflected by the wavelength branch member 10 and a surface image may be acquired on the optical path in which the return light is transmitted. Also in these cases, it is possible to simultaneously acquire an eye fundus surface image and an eye fundus tomographic image in the respective desired regions over a wide angle-of-view range in the same manner as in the first embodiment.

Aspects of the present invention are also achieved by executing the following processing. Specifically, in the processing, a software (program) that achieves the functions of the above embodiments is supplied to a system or an apparatus through a network or various recording media and a computer (or a CPU or MPU) of the system or the apparatus reads the program to execute.

Other Embodiments

Additional embodiments can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present disclosure has been described with reference to exemplary embodiments, it is to be understood that these exemplary embodiments are not seen to be limiting.

This application claims the benefit of Japanese Patent Application No. 2014-199179, filed Sep. 29, 2014, which is hereby incorporated by reference herein in its entirety.

What is claimed is:

1. An ophthalmologic apparatus comprising:
a first light source configured to output first light to be applied to an eye fundus of an eye to be examined;
a first scanning unit configured to scan the eye fundus with the first light;
a second light source configured to output second light having a wavelength different from a wavelength of the first light;
a second scanning unit configured to scan the eye fundus with the second light;
a reflective member configured to reflect light from the first scanning unit and light from the second scanning unit to apply the light from the first scanning unit and the light from the second scanning unit to the eye fundus; and
an optical path synthesis and separation unit arranged on an optical path from the first scanning unit to the reflective member and on an optical path from the second scanning unit to the reflective member, the optical path synthesis and separation unit being configured to synthesize an optical path from the first scanning unit to the eye fundus with an optical path from the second scanning unit to the eye fundus and separate an optical path of return light from the eye fundus into an optical path on which the first scanning unit is arranged and an optical path on which the second scanning unit is arranged,
wherein a reflection optical path of the optical path synthesis and separation unit is arranged opposite to the eye to be examined with respect to the optical path synthesis and separation unit.

2. The ophthalmologic apparatus according to claim 1, wherein
a first focal point of the reflective member is formed in an anterior eye portion of the eye to be examined,
a second focal point of the reflective member is formed in the first scanning unit arranged on a transmission optical path of the optical path synthesis and separation unit, and
a third focal point of the reflective member is formed in the second scanning unit arranged on the reflection optical path of the optical path synthesis and separation unit.

3. The ophthalmologic apparatus according to claim 1, wherein the reflective member is an elliptical reflective mirror.

4. The ophthalmologic apparatus according to claim 3, wherein an ellipticity a/b of the elliptical reflective mirror satisfies 1.1<a/b<2.4, where a denotes a major axis of the elliptical reflective mirror and b denotes a minor axis of the elliptical reflective mirror.

5. The ophthalmologic apparatus according to claim 1, wherein the optical path synthesis and separation unit is a wavelength separation member configured to separate the wavelength of the first light and the wavelength of the second light.

6. The ophthalmologic apparatus according to claim 1, wherein the optical path synthesis and separation unit is a dichroic mirror.

7. The ophthalmologic apparatus according to claim 6, wherein an angle $\alpha$ between a reflection surface of the dichroic mirror and a straight line passing through the first focal point and the second focal point of the reflective member satisfies $-7° < \alpha < 55°$.

8. The ophthalmologic apparatus according to claim 1, wherein a range of an angle of the first light and the second light entering the eye to be examined is 55° or more.

9. The ophthalmologic apparatus according to claim 1, further comprising:
a first detection unit configured to detect return light from the eye fundus irradiated with light from the first scanning unit by the reflective member; and
a second detection unit configured to detect return light from the eye fundus irradiated with light from the second scanning unit by the reflective member.

10. The ophthalmologic apparatus according to claim 9, further comprising:
a first image forming unit configured to form a first image of the eye fundus on the basis of the return light detected by the first detection unit; and
a second image forming unit configured to form the second image of the eye fundus on the basis of the return light detected by the second detection unit.

11. The ophthalmologic apparatus according to claim 10, further comprising:
a splitting unit configured to split the first light into measurement light traveling to the eye fundus and reference light; and
an interference light generation unit configured to multiplex return light from the eye fundus irradiated with the measurement light with the reference light to generate interference light,
wherein the first detection unit is configured to detect the generated interference light, and
wherein the first image forming unit is configured to form, as the first image, a tomographic image of the eye fundus on the basis of the detected interference light.

12. The ophthalmologic apparatus according to claim 1, wherein the second light source includes a plurality of wavelengths.

13. The ophthalmologic apparatus according to claim 1, wherein the second light source includes a visible wavelength.

14. An optical apparatus comprising:
a first scanning unit configured to scan an object to be examined with first light;
a second scanning unit configured to scan the object to be examined with second light having a wavelength different from a wavelength of the first light;
a reflective member configured to reflect light from the first scanning unit and light from the second scanning unit to apply the light from the first scanning unit and the light from the second scanning unit to the object to be examined; and
an optical path synthesis and separation unit arranged on an optical path from the first scanning unit to the reflective member and on an optical path from the second scanning unit to the reflective member, the optical path synthesis and separation unit being configured to synthesize an optical path from the first scanning unit to the object to be examined with an optical path from the second scanning unit to the object to be examined and separate an optical path of return light from the object to be examined into an optical path on which the first scanning unit is arranged and an optical path on which the second scanning unit is arranged,
wherein a reflection optical path of the optical path synthesis and separation unit is arranged opposite to the object to be examined with respect to the optical path synthesis and separation unit.

15. The optical apparatus according to claim 14, wherein the optical path synthesis and separation unit is a wavelength separation member arranged between the reflective member and the first scanning unit and between the reflective member and the second scanning unit, the wavelength separation member being configured to separate the wavelength of the first light and the wavelength of the second light.

16. The optical apparatus according to claim 14,
wherein the first scanning unit is arranged at a position of a focal point of the reflective member on a transmission optical path of the optical path synthesis and separation unit, and
wherein the second scanning unit is arranged at a position of a focal point of the reflective member on the reflection optical path of the optical path synthesis and separation unit.

17. An optical apparatus comprising:
a reflective member configured to reflect first light and second light having a wavelength different from a wavelength of the first light to apply the first light and the second light to an object to be examined; and
a wavelength separation member arranged between the reflective member and a position of a focal point of the reflective member, the wavelength separation member being configured to separate the wavelength of the first light and the wavelength of the second light,
wherein a reflection optical path of the wavelength separation member is arranged opposite to the object to be examined with respect to the wavelength separation member.

18. The optical apparatus according to claim 17, further comprising:
a first scanning unit arranged at a position of a focal point of the reflective member on a transmission optical path of the wavelength separation member, the first scanning unit being configured to scan the object to be examined with the first light; and
a second scanning unit arranged at a position of a focal point of the reflective member on the reflection optical path of the wavelength separation member, the second scanning unit being configured to scan the object to be examined with the second light.

19. The optical apparatus according to claim 14, wherein the reflective member is an elliptical reflective mirror.

20. The optical apparatus according to claim 14, wherein the wavelength separation member is a dichroic mirror.

* * * * *